United States Patent
McMillan et al.

(10) Patent No.: US 10,332,637 B2
(45) Date of Patent: Jun. 25, 2019

(54) USE OF WEB-BASED SYMPTOM CHECKER DATA TO PREDICT INCIDENCE OF A DISEASE OR DISORDER

(71) Applicant: Battelle Memorial Institute, Columbus, OH (US)

(72) Inventors: Nancy McMillan, Columbus, OH (US); Jingyu Feng, Columbus, OH (US); Kathryn Stamps, Suffolk, VA (US); Robert E. Burr, Salt Lake City, UT (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 136 days.

(21) Appl. No.: 14/180,683

(22) Filed: Feb. 14, 2014

(65) Prior Publication Data

US 2014/0236613 A1  Aug. 21, 2014

Related U.S. Application Data

(60) Provisional application No. 61/765,543, filed on Feb. 15, 2013.

(51) Int. Cl.
*G16H 50/80* (2018.01)

(52) U.S. Cl.
CPC .................. *G16H 50/80* (2018.01)

(58) Field of Classification Search
CPC .................. G06Q 50/22–50/24; G16H 50/80
See application file for complete search history.

(56) References Cited

U.S. PATENT DOCUMENTS

| 7,840,421 B2 | 11/2010 | Gerntholtz |
| 2006/0036619 A1* | 2/2006 | Fuerst .................. G06F 19/3443 |
| 2008/0021288 A1* | 1/2008 | Bowman ............... G06F 19/322 600/300 |
| 2008/0208624 A1* | 8/2008 | Morita .................. G06F 19/322 705/2 |
| 2010/0168540 A1 | 7/2010 | Kamath et al. |

(Continued)

OTHER PUBLICATIONS

Ginsberg et al. "Detecting influenza epidemics using search engine query data". Nature vol. 457, Feb. 19, 2009.*

(Continued)

*Primary Examiner* — Elaine Gort
*Assistant Examiner* — Devin C Hein
(74) *Attorney, Agent, or Firm* — Fay Sharpe LLP (57) ABSTRACT

Symptoms and methods for predicting the incidence of a disease or disorder are disclosed. A system for predicting the incidence of a disease or disorder includes a web-based symptom checker for producing a structured dataset, a data analysis component for producing a multivariate dataset from the structured dataset, and a feature construction component for producing a linear combination of orthogonal symbols representative of a disease or disorder. A method for predicting the incidence of a disease or disorder includes producing a multivariate dataset representing patient symptom counts, performing feature construction analysis on the multivariate dataset, creating a time series model using weekly illness incidence data, and applying the time series model to new illness incidence data to predict the incidence of a disease or disorder in the future.

22 Claims, 11 Drawing Sheets

(56) References Cited

U.S. PATENT DOCUMENTS

2011/0093249 A1    4/2011  Holmes et al.
2013/0031041 A1*  1/2013  Maciejewski .......... G06Q 10/10
                                                          706/46
2013/0031179 A1*  1/2013  Christakis ............. G06Q 10/10
                                                          709/204

OTHER PUBLICATIONS

Johnson, H. A. et al., Analysis of Web Access Logs for Surveillance of Influenza, 2004, In Medinfo, 1202-1206 (Year: 2004).*
International Search Report for corresponding PCT Application No. PCT/US2014/016411 dated May 13, 2014.

* cited by examiner

Parameter Estimates

| Variable | DF | Estimate | Standard Error | t Value | Approx Pr > \|t\| |
|---|---|---|---|---|---|
| Intercept | 1 | -0.0860 | 0.0141 | -6.10 | <.0001 |
| Prin1 | 1 | -0.0239 | 0.006073 | -3.94 | 0.0004 |
| Prin2 | 1 | -0.0247 | 0.009504 | -2.60 | 0.0143 |
| Prin4 | 1 | 0.0451 | 0.0186 | 2.43 | 0.0213 |
| Prin9 | 1 | 0.1425 | 0.0628 | 2.27 | 0.0304 |
| AR3 | 1 | -0.0105 | 0.1631 | -0.06 | 0.9491 |
| AR4 | 1 | 0.4124 | 0.1736 | 2.38 | 0.0238 |

USE OF WEB-BASED SYMPTOM CHECKER DATA TO PREDICT INCIDENCE OF A DISEASE OR DISORDER

This application claims the benefit of U.S. Provisional Application No. 61/765,543 filed Feb. 15, 2013. U.S. Provisional Application No. 61/765,543 filed Feb. 15, 2013 is incorporated herein by reference in its entirety

BACKGROUND

The present disclosure relates to systems and methods for the early detection and characterization of outbreaks of infectious diseases or disorders. Generally, the system may be used for capturing and analyzing web-based patient symptom queries to thereby predict future changes in the incidence of infectious illness in both time and location. Methods to predict the incidence of disease or disorders are also disclosed.

In public health practice, the earliest detection of a disease outbreak offers the best opportunity to mitigate its effects. Consequently, one of the core functions of public health surveillance is to monitor public health status and recognize at the earliest possible time, the appearance of disease or a change in its distribution or incidence. To address that need, various methods of early detection are incorporated throughout the public health infrastructure at all levels from local to national. Depending on the specific microbiological etiology of the outbreak, this early intervention allows for early recognition of affected individuals, initiation of treatment, and initiation of post-exposure mitigations among the exposed population. Accordingly, prediction technologies should offer the earliest reliable detection and characterization of outbreaks to afford the greatest opportunity to minimize causalities.

Traditional systems of public health surveillance, developed and managed by public health agencies at various jurisdictional levels from local to national, fall into two categories: passive and active. Passive systems rely on reporting from community based healthcare personnel, whether from clinical encounters or laboratory identification of select microorganisms. These systems generally under-report infectious disease incidence and prevalence, and are only as timely as the reporters. Recognizing the limitations of the passive systems, public health surveillance authorities have developed active systems that prospectively monitor for the appearance of diseases and pathogens. These systems can identifying the appearance of pathogens in the environment earlier than passive surveillance systems, but are limited still in their scope. However, they are also directed against specific agents and illnesses, and active systems that are based on environmental monitoring have their own inherent time delays between the appearance of a pathogen and its recognition in the surveillance system due to time delays for laboratory analysis.

A substantial number of active surveillance systems have been developed. Some of these systems exploit search engines such as Google and Yahoo. The Internet, more specifically social media, is growing as a resource to gain advice or chat about health conditions. Microblogging sites like Twitter and Facebook or search engines such as Google collect random entries about conditions affecting its users.

The best developed active surveillance system on the national scale is the CDC's system for influenza. It provides a clear picture of the emergence and development of the annual influenza epidemic, but its reports lag the actual changes in influenza incidence by about a week. The reason for the lag is that the system depends on the reporting of medical visits by specific sentinel medical practices, of individuals ill with symptoms compatible with influenza. It requires that individuals become ill enough to request an appointment and wait for that appointment to occur before there is the possibility of a report being generated.

Recognizing the time delays inherent in surveillance systems based on the data generated by clinical visits and the critical importance of detecting the earliest possible evidence of an outbreak, there have been a number of methods proposed to accelerate reporting. Many of these are based on examining information from individuals who may be developing illness, eliminating the additional steps required to seek medical care and generate a medical report. All these techniques exploit one aspect or another of the public's use of the Internet to report or obtain information. Others have used medical query sites maintained by hospitals or health departments, emergency rooms or pharmacy visits.

BRIEF DESCRIPTION

In one illustrative embodiment, a system for predicting the incidence of a disease or disorder includes a web-based symptom checker for producing a structured dataset, a data analysis component for producing a multivariate dataset from the structured dataset, a principle component analysis component for producing a linear combination of orthogonal symbols representative of a disease or disorder, and a multivariate statistical model for predicting the incidence of disease or disorder using the symbols constructed from the principal component analysis.

In another illustrative embodiment, a method for predicting the incidence of a disease or disorder includes producing a multivariate dataset representing Internet symptom counts, performing principle component analysis on the multivariate dataset, creating a time series model using weekly illness incidence data and principal components of Internet symptom data, and applying the time series model to new Internet symptom data to predict the incidence of a disease or disorder.

BRIEF DESCRIPTION OF THE DRAWINGS

The following is a brief description of the drawings, which are presented for the purposes of illustrating the exemplary embodiments disclosed herein and not for the purposes of limiting the same.

These figures are merely schematic representations based on convenience and the ease of demonstrating the existing art and/or the present development, and are, therefore, not intended to indicate relative size and dimensions of the assemblies or components thereof.

DETAILED DESCRIPTION

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

Prediction systems for detecting the incidence of a disease or disorder according to the present disclosure may capture patient-based symptom queries to a public symptom search engine in its clinician-informed database of disease symptoms. This database may then be analyzed at or near real-time to detect changes in the incidence of inquiries related to infectious illness syndromes in terms of both time and location. At the end of the development process, the prediction system may be validated against real outbreak data in order to demonstrate its real-world performance.

The systems and methods according to the following disclosure may include: 1) Evaluation of events in (near) real-time; 2) The ability to discriminate meaningful information from background noise with adequate sensitivity to provide useful early detection and; 3) The ability to provide geographical and temporal characteristics of an event (i.e., where it is centered, the likely extent, speed of spread, and the characteristics of illness that indicate specific causes).

It is recognized herein that any major public system based on Internet usage has a limited window of maximum utility, which occurs very early and very briefly in an event. Once there is public knowledge of an outbreak, the parameters of public interaction change, and affect the ability of any analytic system based on evaluating Internet data to reach reliable assessments of the important characteristics of the outbreak. It is precisely this early and limited window of patient queries that will allow a predictive system to accurately and reliably provide early warning and detection of an outbreak. Furthermore, the disclosed systems and methods may utilize a stronger dataset (e.g. structured, targeting medically relevant symptoms) than other public systems like Google, and will lead the 'reliability race' because of the sheer number and type of queries in a structured dataset, such as the data generated by on-line symptom checking diagnostic tools (OLSC-DT) like WebMD's Symptom Checker (at http://www.webmd.com/) or iTriage (https://www.itriagehealth.com/#!/avatar). Because data from OLSC-DT can be structured data already filtered to health-related data (rather than the world of search queries provided by Google) and because geo-location (using both IP and user-inputted zip codes) and time tags can be collected by OLSC-DT, predictive systems and methods using this dataset are expected to provide greater reliability in detection as compared with data mined from unstructured sources.

Figure 1:
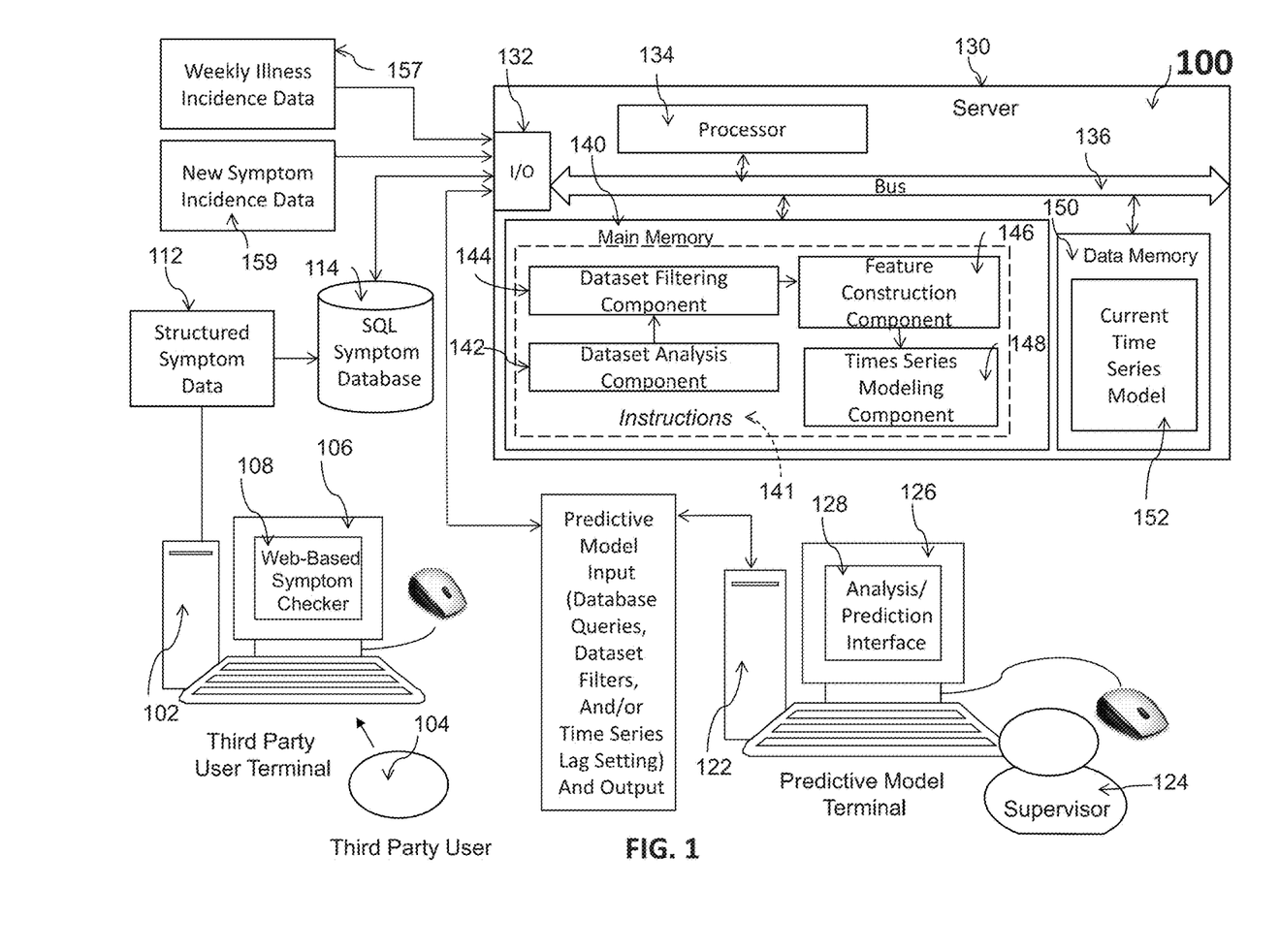
FIG. 1 is an overview diagram of a system for predicting the incidence of a disease or disorder according to a first exemplary embodiment.

With reference to FIG. 1, a system 100 for predicting the incidence of a disease or disorder according to a first exemplary embodiment includes at least one third party side and a supervisor side. In one embodiment, there are a plurality of third party sides and one supervisor side. The number of third party sides depends on the number of users reporting symptoms of a disease or disorder to the symptom checker website. At the third party side, a third party user 104 (i.e., a person experiencing symptoms of illness and utilizing the symptoms checker website) inputs data into a third party user terminal 102 (e.g. a computer, tablet computer, or other device running a web browser connected with the symptoms checker website, although other terminal devices such as a dedicated "dumb" terminal are also contemplated). The user 104 views a display 106 attached to the terminal 102 so that a web-based symptom checker website 108 may be engaged by the user 104. The user 104 inputs symptom specific data into the website 108 using a dialog, preferably a graphical user interface (GUI) dialog, such as a web form presenting lists of symptoms and checkboxes via which the user identifies the symptoms present in the user. Some symptoms may be entered using other GUI dialogs which enable entry of quantitative data, e.g. body temperature as measured by an oral thermometer, body weight, et cetera. Other GUI dialogs are also contemplated. The resulting data are organized as a structured data set for the user 104. In some illustrative embodiments, however, the specific user-symptom association is not maintained, but rather the data for the purpose of disease tracking are output as a structured symptom dataset 112 containing individual user 104 symptom counts, each symptom count associated with a time stamp and geographical designation. This approach loses relevant information pertaining to co-occurrence of symptoms in a single user; however, it has advantages in enhanced data processing efficiency, reduced data storage requirements, and elimination of certain potential medical information privacy issues. The structured dataset 112 may include demographic information, such as the age, gender, and zip code of the user 104. It may also include specific symptoms selected by the user 104, body location, qualifiers or follow-up questions to symptoms, or possible conditions based on algorithms using symptom qualifiers. The structured dataset 112 is uploaded to a SQL symptom database 114 and stored on a server 130.

On the supervisor side, a supervisor 124 inputs data into a predictive model terminal 122. The supervisor views a display 126 attached to the terminal 122 so that an analysis/prediction interface 128 may be engaged by the supervisor 124. The input provided by the supervisor 124 at the predictive model terminal 122 includes select database queries or other filters for creating subsets of data within a server 130 using data from the SQL symptom database 114. The input may also include a time series lag setting, which is utilized by the server 130 in creating time series models.

The server 130 includes an input/output module 132 which receives input from the third party user terminal 102 and predictive model terminal 122, as well as past weekly (or other chosen time interval) illness incidence data 157 and new symptom incidence data 159. The illness incidence data 157, may be obtained by any reporter agency or sentinel provider that collects counts of symptom incidents associated with a disease or disorder. For example, in the United States the Centers for Disease Control (CDC) collects data associated with influenza like illness (ILI). The CDC defines ILI by the symptoms of fever (equal to or greater than 100°) and cough and/or sore throat. The CDC collects its data from sentinel providers across the country.

Figure 3:
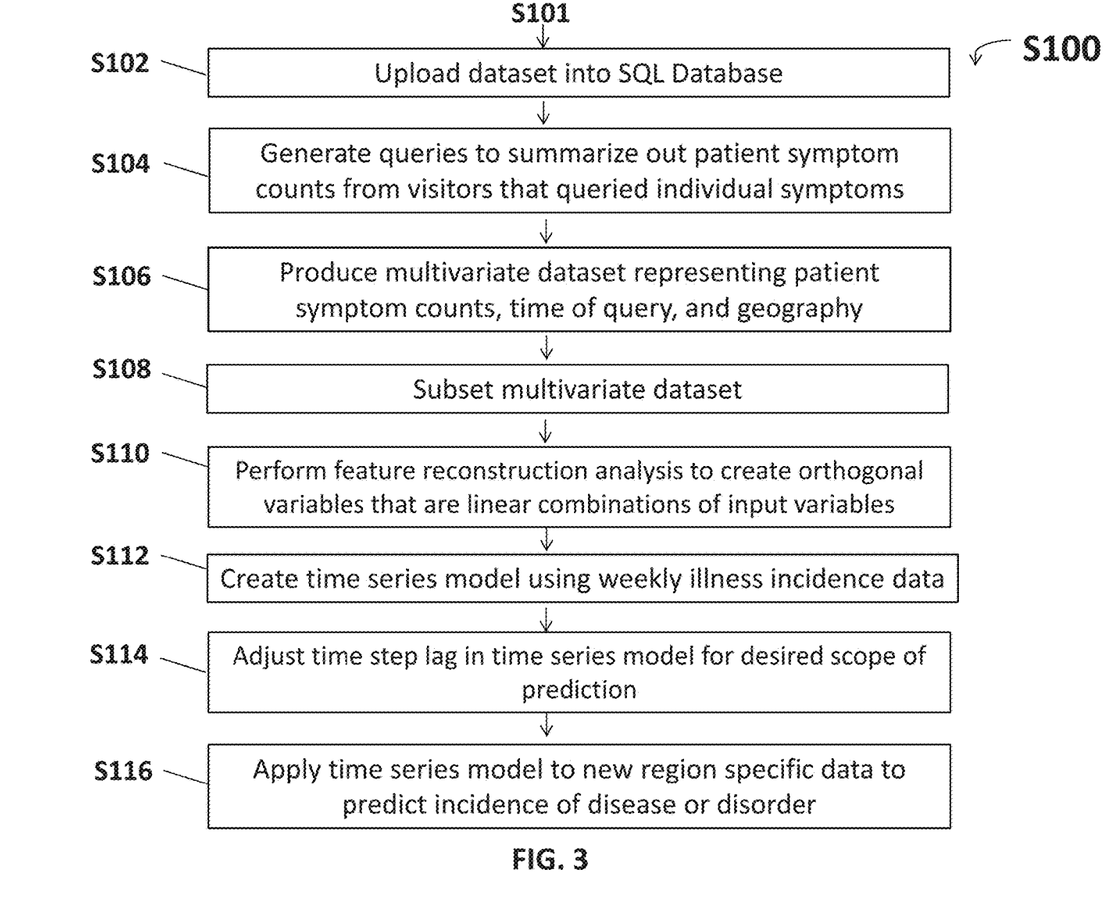
FIG. 3 is a method for predicting the incidence of a disease or disorder.

The illustrative server computer 130 may include main memory 140 which stores instructions 141 for implementing the exemplary method described with respect to FIG. 3, and a processor 134, in communication with the memory 140, for executing the instructions 141. Hardware components 132, 134, 140, and 150 may communicate via a data/control bus 136.

In an exemplary embodiment, the main memory 140 stores a dataset analysis component 142 for creating a multivariable dataset from data within the SQL symptom database 114. (While a SQL database is employed in the illustrative examples, other data storage/processing systems are also contemplated). A dataset filtering component 144 creates subsets within the multivariable dataset based on, e.g., physician advice as to the most important symptoms, or other inputs provided by the supervisor 124 at the predictive model terminal 122. (Alternatively, such feature selection may be "front-ended", e.g. performed during construction of the structured symptom data set 112 by only storing the chosen subset of symptoms as the data set 112). A feature construction component 146 operates on the multivariate dataset to make the dataset more amenable to future time series modeling. In one embodiment, the feature construction component 146 is a principal component analysis (PCA) component 146. The PCA component 146 performs principal component analysis on the subsets (or filtered multivariable dataset) to produce a linear combination of orthogonal variables. Other methods are contemplated for the construction of feature vectors from the structured symptom data set. A time series modeling component 148 creates a time series model. The time series model may be dependent upon the output of the feature construction component 146 and weekly illness incidence data 157.

The illustrative server 130 also includes a data memory 150 which stores the most current time series model 152 calculated by the time series modeling component 152. The current time series model 152 is stored in data memory 150 to predict the incidence of new disease or disorder occurrences in a designated future (e.g. week-ahead) time interval based on the time series model 152 applied to new symptom incidence data 159 and historic weekly incidence data 157.

The server computer memory 140, 150 may be separate or combined and may represent any type of non-transitory computer readable medium such as random access memory (RAM), read only memory (ROM), magnetic disk or tape, optical disk, flash memory, or holographic memory. In one embodiment, the memory 140, 150 comprises a combination of random access memory and read only memory. In some embodiments, the processor 134 and memory 140 and/or 150 may be combined in a single chip. The input/output module 132 allows the computer to communicate with other devices via a computer network, such as a local area network (LAN) or wide area network (WAN), or the Internet, and may comprise a modulator/demodulator (MODEM), wired Ethernet, wireless WiFi, or so forth.

The digital processor 134 can be variously embodied, such as by a single-core processor, a dual-core processor (or more generally by a multiple-core processor), a digital processor and cooperating math coprocessor, a digital controller, or the like. The digital processor 134, in addition to controlling the operation of the server computer 130, executes instructions 141 stored in memory 140 for performing the method outlined in FIG. 3.

The third party user terminal 102 and predictive model terminal 122 may be similarly configured to the server computer 130 and may each comprise one or more specific or general purpose computing devices, such as a PC, such as a desktop, a laptop, palmtop computer, portable digital assistant (PDA), server computer, cellular telephone, tablet computer, pager, combination thereof, or other computing device capable of executing instructions for performing the client side operations of the exemplary method. The third party user terminal 102 and predictive model terminal 122 may have memory, a processor, and an input/output device for communicating with other devices via the network. The third party user terminal 102 and predictive model terminal 122 may also include an agent user input device, analogous to user input device, such as a keyboard, keypad, touchscreen, cursor control device, or combination thereof, or the like, for inputting commands to the respective processor.

The term "software," as used herein, is intended to encompass any collection or set of instructions executable by a computer or other digital system so as to configure the computer or other digital system to perform the task that is the intent of the software. The term "software" as used herein is intended to encompass such instructions stored in storage medium such as RAM, a hard disk, optical disk, or so forth, and is also intended to encompass so-called "firmware" that is software stored on a ROM or so forth. Such software may be organized in various ways, and may include software components organized as libraries, Internet-based programs stored on a remote server or so forth, source code, interpretive code, object code, directly executable code, and so forth. It is contemplated that the software may invoke system-level code or calls to other software residing on a server or other location to perform certain functions.

Figure 2:
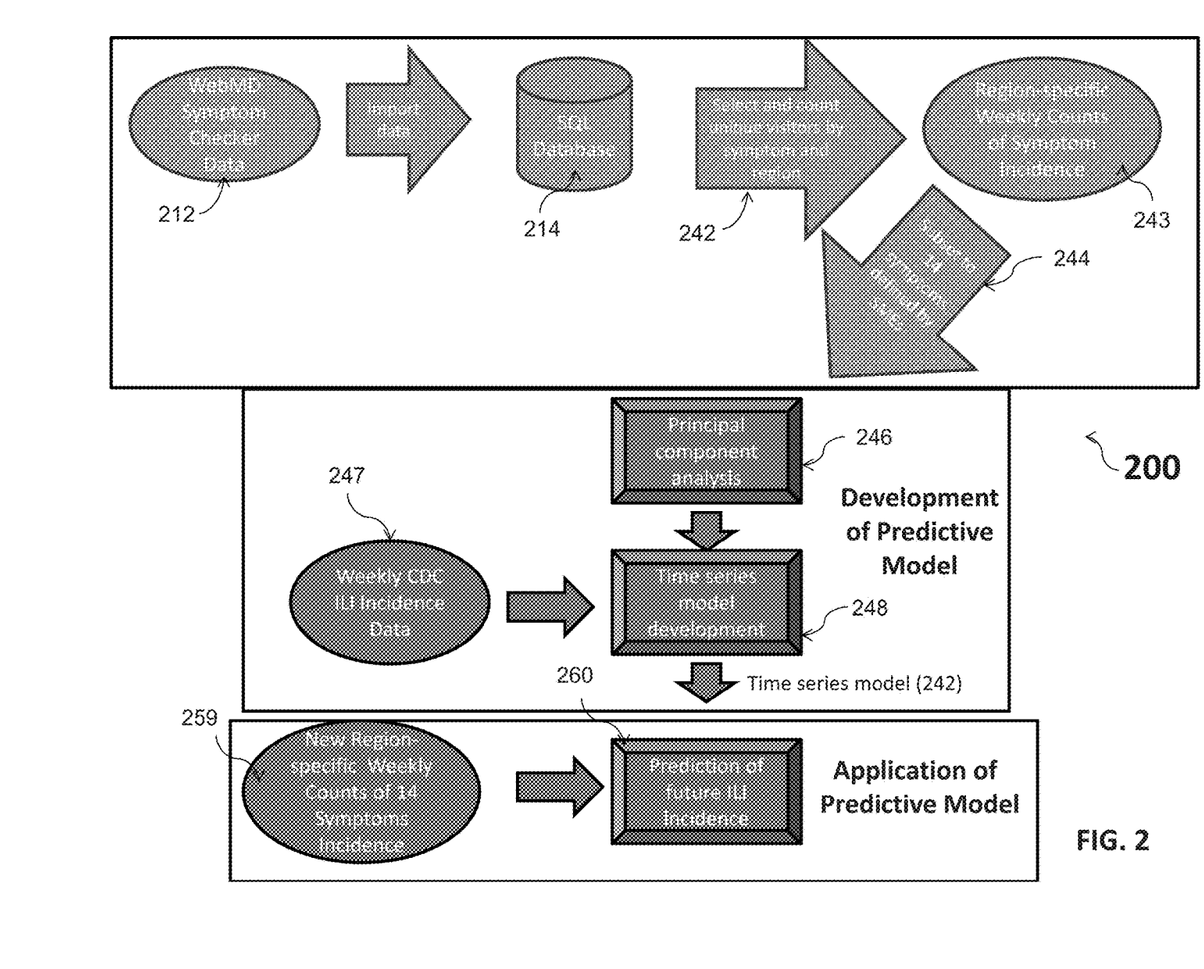
FIG. 2 is a block flow diagram for a system for predicting the incidence of influenza like illness (ILI) according to a second exemplary embodiment.

With reference to FIGS. 2 and 3, a system 200 for predicting the incidence of a disease or disorder suitably implemented using hardware such as that described with reference to FIG. 1 uses OLSC-DT data 212. The OLSC-DT data has substantial advantages for disease occurrence tracking because users input their symptoms using a web form or other dialog specifically configured to elicit symptom information, obviating the need for text interpretation or other data mining operations, and decreasing the number of misleading queries. Many of these systems, such as WebMD's Symptom Checker are tied to health information services, which provide users with additional information on medical conditions and topics. These systems maintain customized portal, which walk users through a series of questions answered through the click of a button or selection from drop-down lists about the body location and specific symptoms with qualifying information such as intensity or character of pain. Based on the information entered, the user is directed to seek emergency care and/or shown a list of possible causes. Some of these systems, like the WebMD Symptom Checker, also collect additional parameters, such as gender, age, date, time, and geographical locations through zip code entry and user Internet protocol (IP) address. Analysis of these data, which specifically utilizes queried symptoms, can look at changes in the incidence and frequencies of symptom queries and trends over time, and by location, for various conditions to determine if there are potential spikes in illnesses or disease conditions.

Preparation of the system 200 includes the OLSC-DT data 212 being imported to a SQL database 214. The data 212 is then selected and counted by unique visitors by symptom and region by dataset analysis component 242. A region-specific weekly counts of symptom incidence multivariable data set 243 is produced. The dataset 243 is filtered into one or more subsets defined by subject matter expertise (SME, e.g. influenza-relevant symptoms identified by medical experts) by a dataset filtering component 244. In the exemplary embodiment, 14 subsets are used representing 14 important symptoms for influenza like illness (ILI).

Development of the system 200 includes the filtered dataset being used for principal component analysis (PCA) by a PCA component 246. Other feature construction methods, such as partial lease squares regression, are contemplated for constructing feature vectors. The output of the PCA component 246 may subsequently be used along with weekly CDC ILI Incidence data 247 by a time series model component 248 to produce a time series model 248. The second exemplary embodiment system 200 differs from system 100 in that weekly illness incidence data is specifically obtained from the CDC and the symptom query data is subset to include only symptoms involved in influenza like illness (ILI).

Application of the predictive system 200 includes applying the time series model 248 to new specific weekly counts of symptoms incidence 259 to create a future prediction of ILI incidence 260.

With particular reference to FIG. 3, a method for predicting the incidence of a disease or disorder starts at S101. At S101, a dataset is uploaded into a SQL database. At S104, queries are generated to summarize-out patient symptom counts from visitors that queried individual symptoms. At S106, a multivariate dataset is produced representing patient symptom counts, time of queries, and/or geography, which may or may not include originating I.P. address. At S108, the multivariate dataset is subset based on, e.g. algorithms, manually input filters, expert medical device regarding the important predictive factors associated with the particular disease being predicted, etc. At S110, a principal component analysis or other multivariate feature construction algorithm is performed to create orthogonal variables that are linear combinations of input variables. At S112, a time series model is created using weekly illness incidence data. At S114, the time step lag in a time series model is adjusted based on the desired scope of prediction. At S116, the time series model is applied to new region specific data showing incidence of a disease or disorder to predict the incidence of a new disease or disorder.

The method of FIG. 3 may be implemented on one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphical card CPU (GPU), or PAL, or the like, e.g. on the hardware described with reference to FIG. 1. In general, the method illustrated in FIG. 3 may be implemented in a computer program product or products that may be executed on a computer. The computer program product may be a non-transitory computer-readable recoding medium on which a control program is recorded, such as a disk, hard drive, or the like configured for performing the method. Common forms of computer-readable media include, for example, floppy discs, flexible discs, hard disks, magnetic tape, or any other magnetic storage medium, CD-ROM, DVD, or any other optical medium, a RAM, a PROM, an EPROM, a FLASH-EPROM, or other memory chip or cartridge, or any other non-transitory medium from which a computer can read and use. The computer program product may be integral with the server computer 130, (for example, an internal hard drive of RAM), or may be separate (for example, an external hard drive operatively connected with the server computer 130), or may be separate and accessed via a digital data network such as a local area network (LAN) or the Internet (for example, as a redundant array of inexpensive of independent disks (RAID) or other network server storage that is indirectly accessed by the server computer 130, via a digital network).

Alternatively, the method may be implemented in transitory media as a transmittable carrier wave in which the control program is embodied as a data signal using transmission media, such as acoustic or light waves, such as those generated during radio wave and infrared communications, and the like.

Various aspects of the method S100 will now be described in greater detail:

S102 and S104: Upload Dataset and Generate Queries

Figure 4:
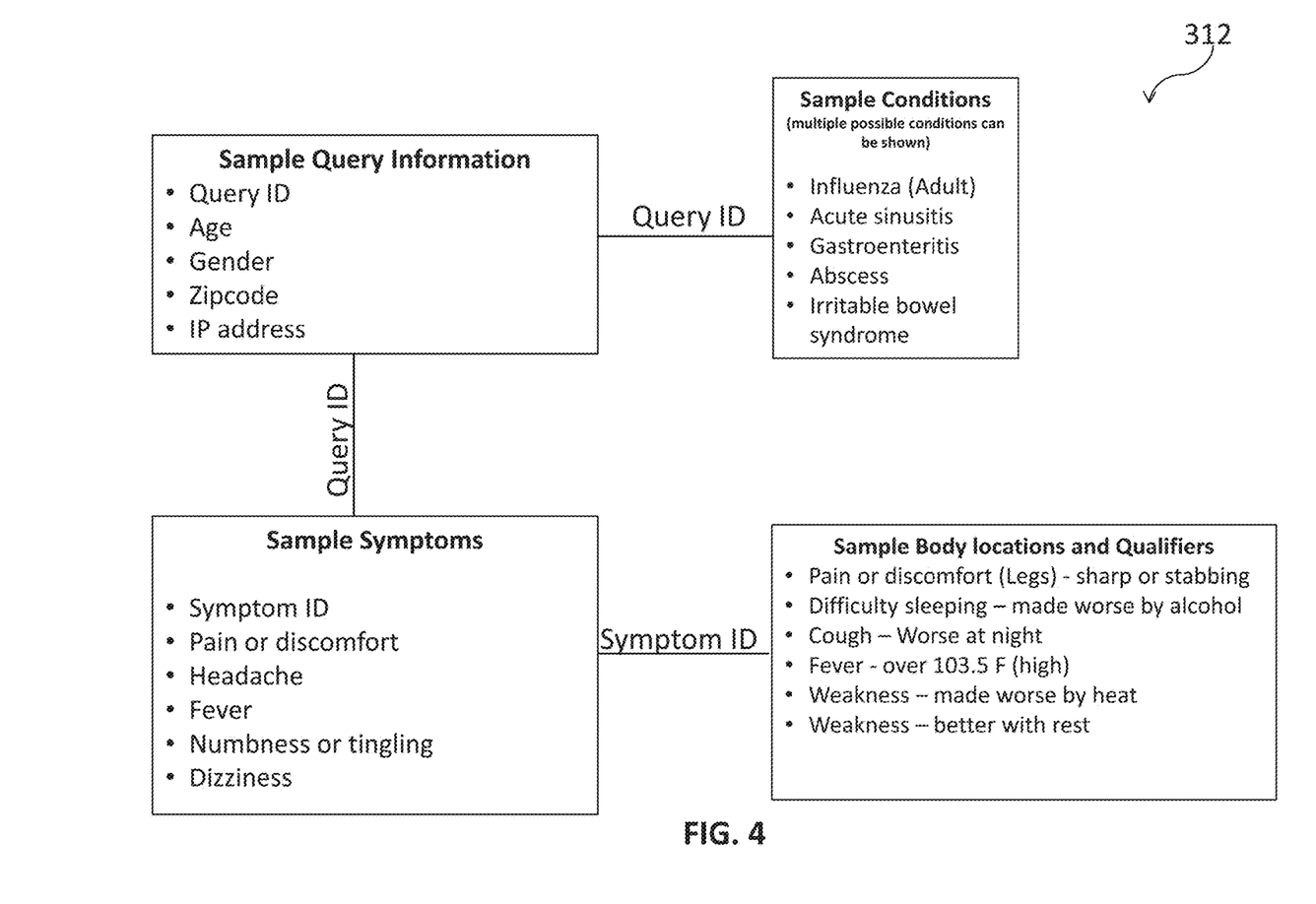
FIG. 4 is an overview diagram of a structured web-based symptom checker dataset.

With reference to FIG. 4, a structured dataset such as that collected by WebMD Symptom checker categorizes data into numerous categorizes, such as Query Information, Symptoms, Body Locations and Qualifiers, and Conditions. A variable number of symptoms may be associated with each query; a variable number of body locations and qualifiers may be associated with each symptom; a variable number of conditions may be associated with each query.

A structured dataset such as the dataset described in FIG. 4 is uploaded to a SQL server for further refinement by generated queries. Queries may reduce the dataset to, e.g., a specific number of predictive symptoms.

S112: Create Time Series Model Using Weekly Illness Incidence Data

Figure 5:
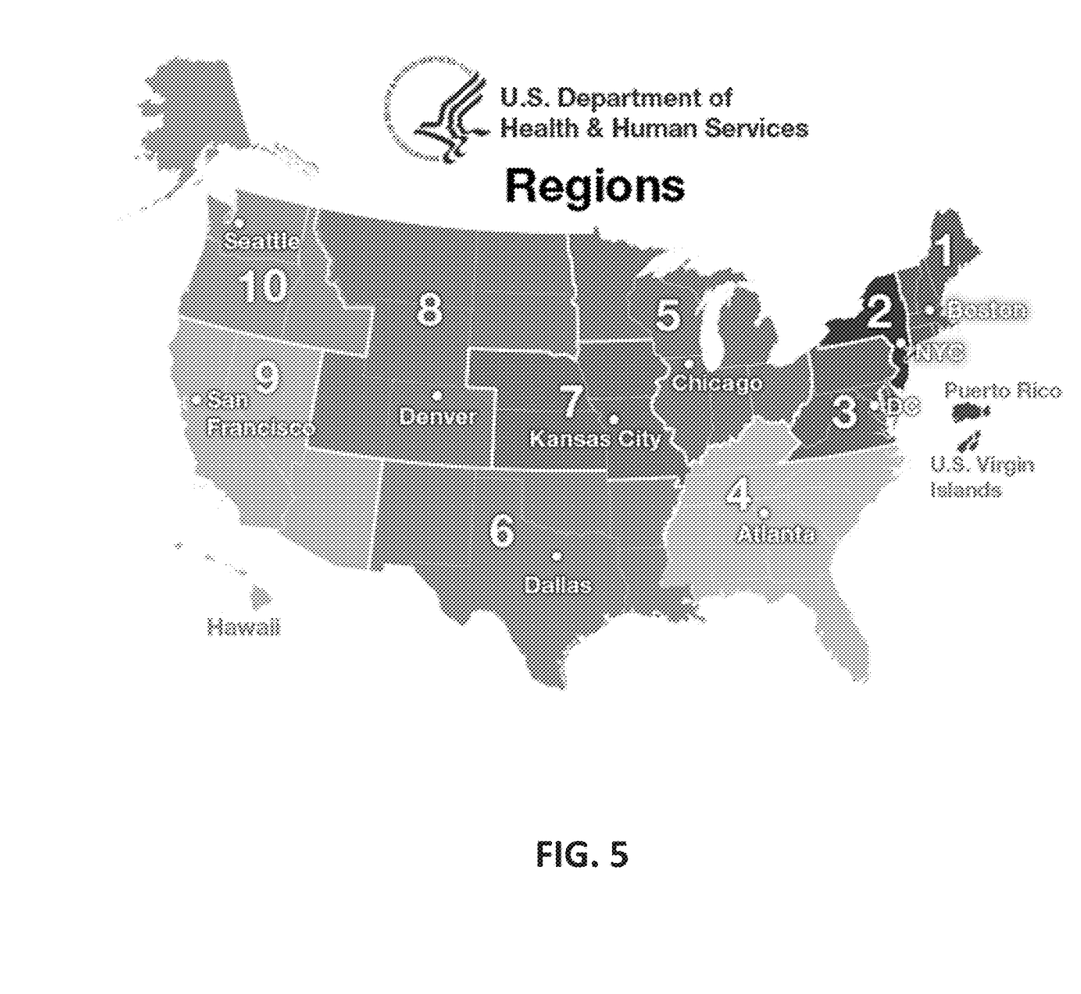
FIG. 5 is a diagram of Health and Human Services (HSS) Regions.

With reference to FIG. 5, weekly illness incidence data may be obtained from any reporter agency or sentinel provider that collects counts of symptom incidents associated with a disease or disorder. In one embodiment, CDC ILI Data is used. The CDC collects data associated with influenza like illness (ILI) data from sentinel providers across the country and reports it according to regions defined by the Health and Human Services (HHS). The CDC specifically defines ILI by the symptoms of fever (equal to or greater than 100°) and cough and/or sore throat. Any number of HHS regions may be used in creating the time series model.

Figure 6:
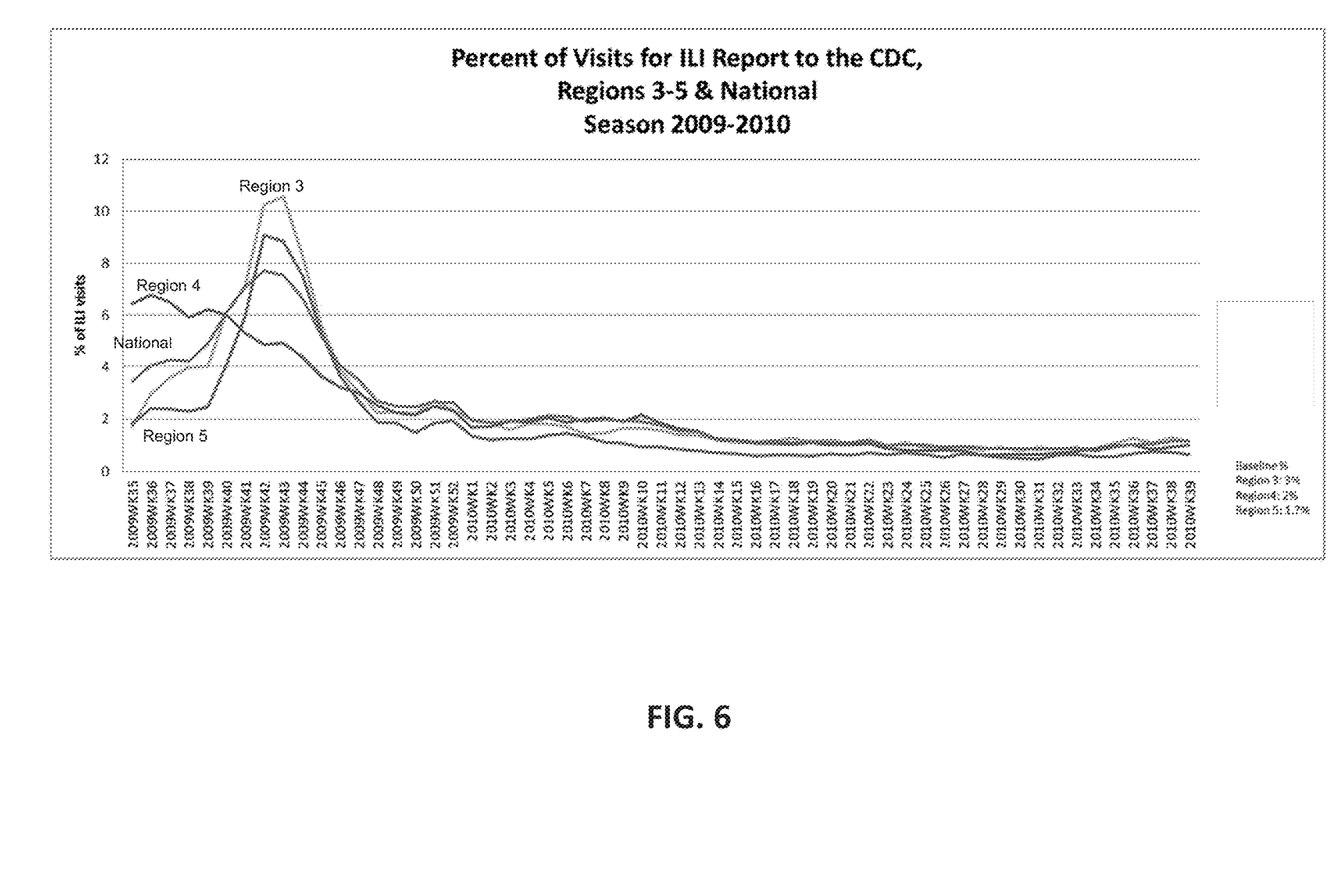
FIG. 6 is a graph of CDC (Center of Disease Control) ILI Data for the 2009-2010 flu season for HSS Regions 3, 4, 5, and national.

With reference to FIG. 6, the percent of visits for ILI reported data to the CDC representing regions 3-5 and national flu season 2009-2010 is shown. With cross reference to FIG. 5, region 3 corresponds to Delaware, District of Columbia, Md., Pennsylvania, Virginia, and West Virginia. Region 4 corresponds to Alabama, Florida, Georgia, Kentucky, Mississippi, North Carolina, South Carolina, and Tennessee. Region 5 corresponds to Illinois, Indiana, Michigan, Minnesota, Ohio, and Wisconsin.

Figure 7:
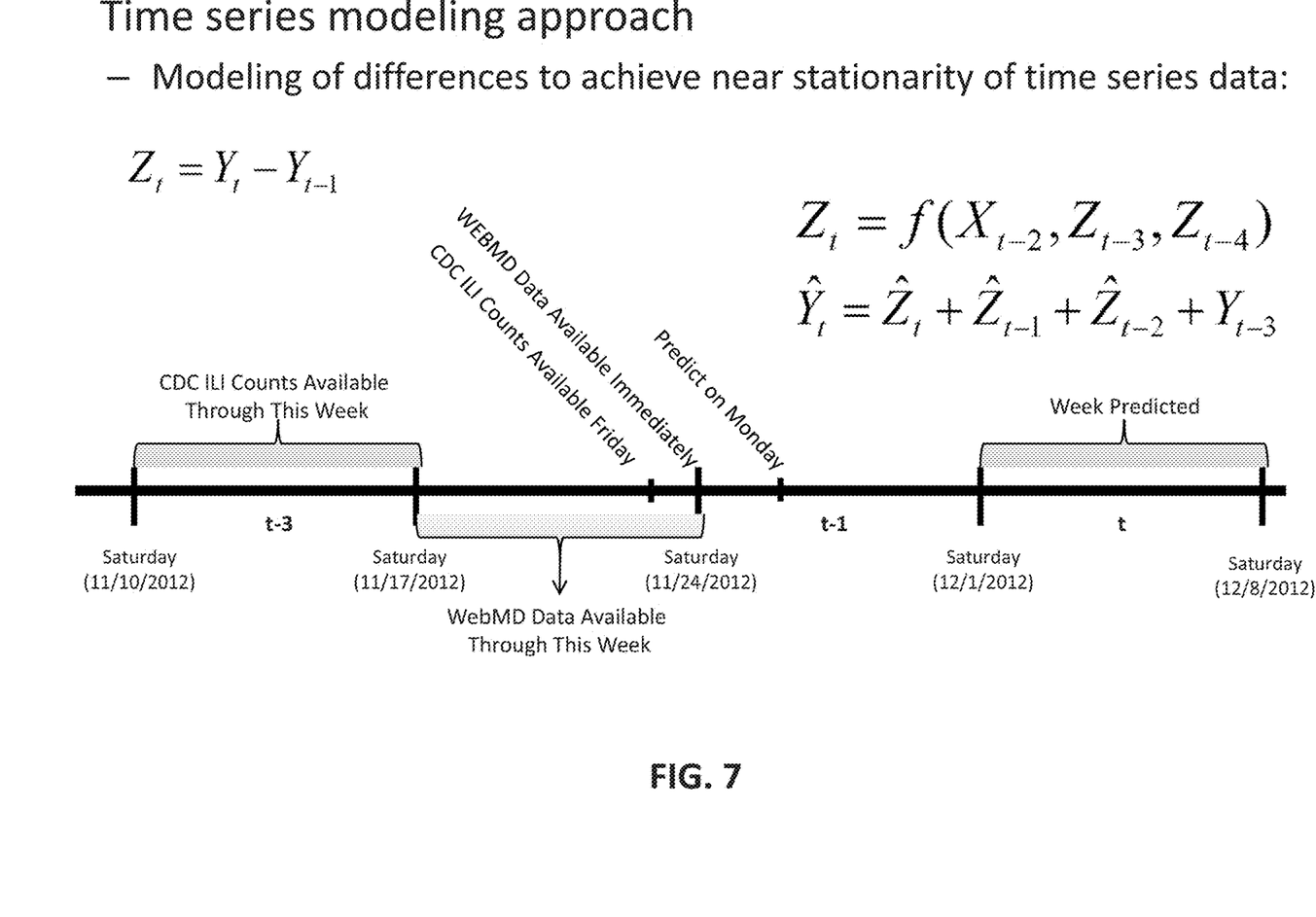
FIG. 7 is a timeline illustration of the time series modeling approach used in the system and methods of FIGS. 1-3.

With reference to FIG. 7, a time series modeling approach includes modeling of differences to achieve near stationarity of time series data. Lagged differences of CDC ILI Count data, such as that represented in FIGS. 5-6, may be used in a time series modeling approach (Z variables with subscripts $t-3$ and $t-4$) in the equations illustrated in FIG. 7. Symptom query features, such as those constructed by principal component analysis are used in the modeling approach (X variables with subscript $t-2$) in the equations illustrated in FIG. 7. In one embodiment, CDC ILI counts may be predicted up to two weeks ahead (represented by t, week predicted) according to the time series modeling approach. Specific dates shown on the timeline presented in FIG. 7 are for illustrative purposes only.

EXAMPLES

With reference to FIGS. 8-11, WebMD symptom counts were constructed. Each unique visitor within a postal code within HHS Region 3 who entered a particular symptom was counted. The significance of each symptom was assessed individually in a time series model according to FIG. 7. Fourteen symptoms were considered: (1) Body aches or pains, (2) chills, (3) cough, (4) diarrhea, (5) difficulty breathing through nose, (6) fatigue, (7) fever, (8) headache, (9) headache (worst ever), (10) joint's ache, (11) nausea or vomiting, (12) runny nose, (13) shaking chills (rigors), (14) sore throat.

Figure 8:
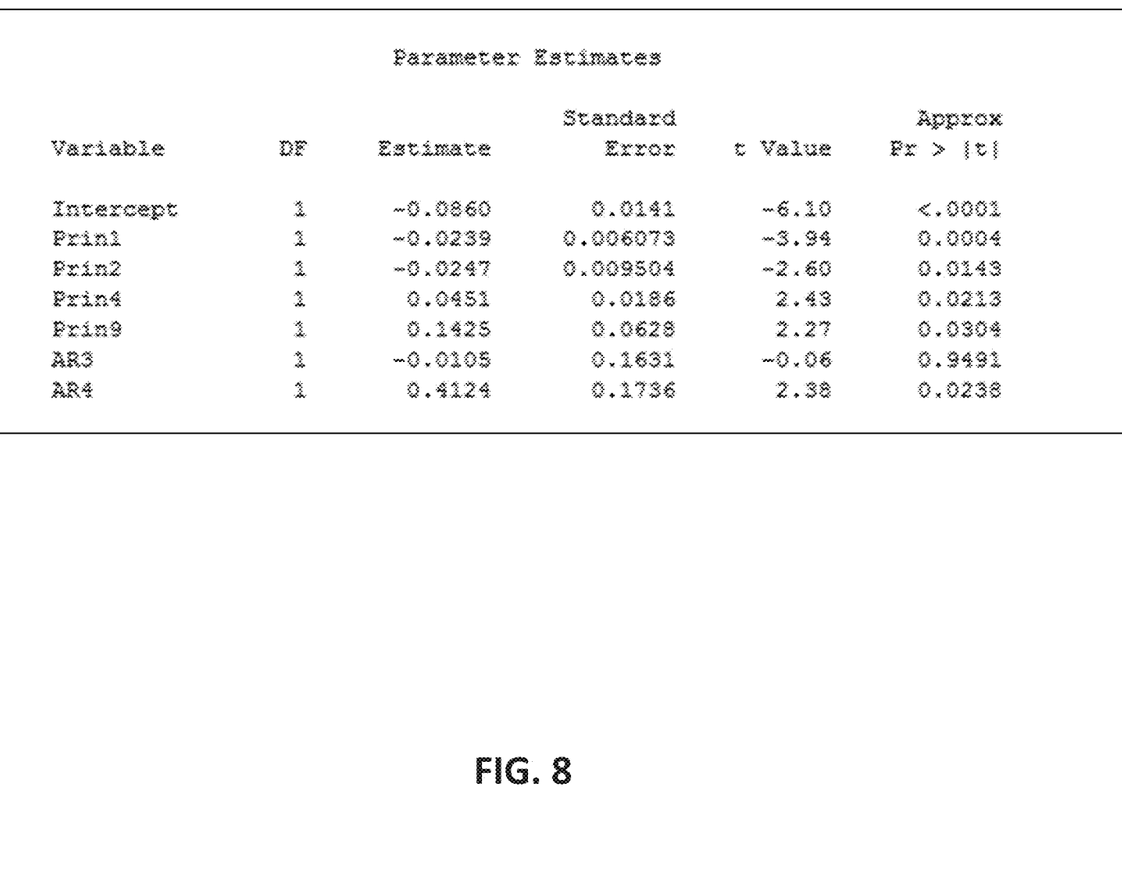
FIG. 8 is a table of principal component analysis (PCA) parameter estimates indicating the most statistically significant predictor components (PCs) for predicting CDC ILI counts using the system according to the second exemplary embodiment shown in FIG. 2.

Principle component analysis (PCA) was performed on the symptom counts identified as possible predictors of CDC ILI counts listed above. With reference to FIG. 8, the $1^{st}$, $2^{nd}$, $4^{th}$, and $9^{th}$ PCs were statistically significant predictors of CDC ILI counts. $R^2=0.51$ (without WebMD data, $R^2=0.02$).

Figure 9:
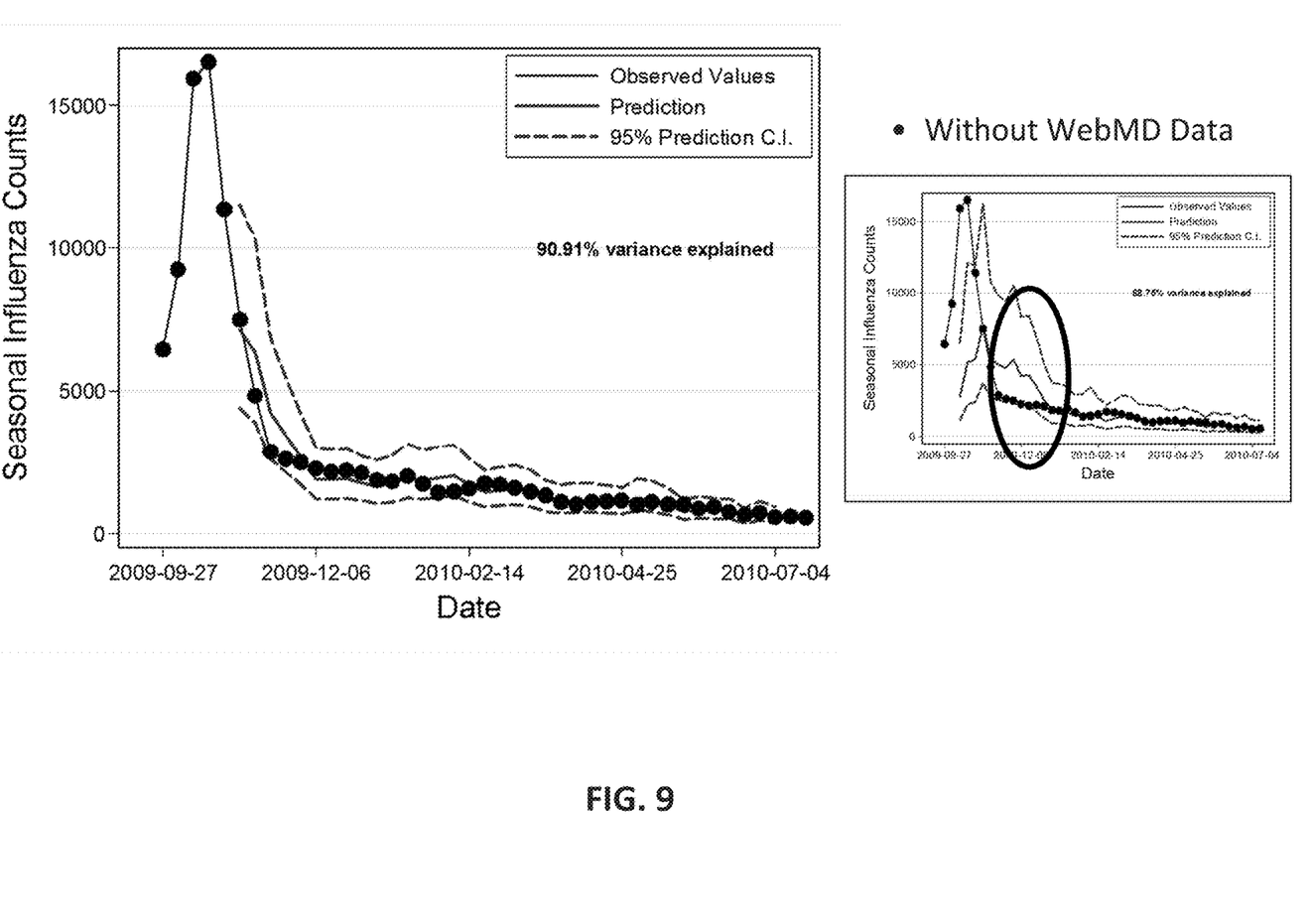
FIG. 9 is a graph of the prediction performance of the system according to the second exemplary embodiment shown in FIG. 2 in HHS Region 3.
Figure 10:
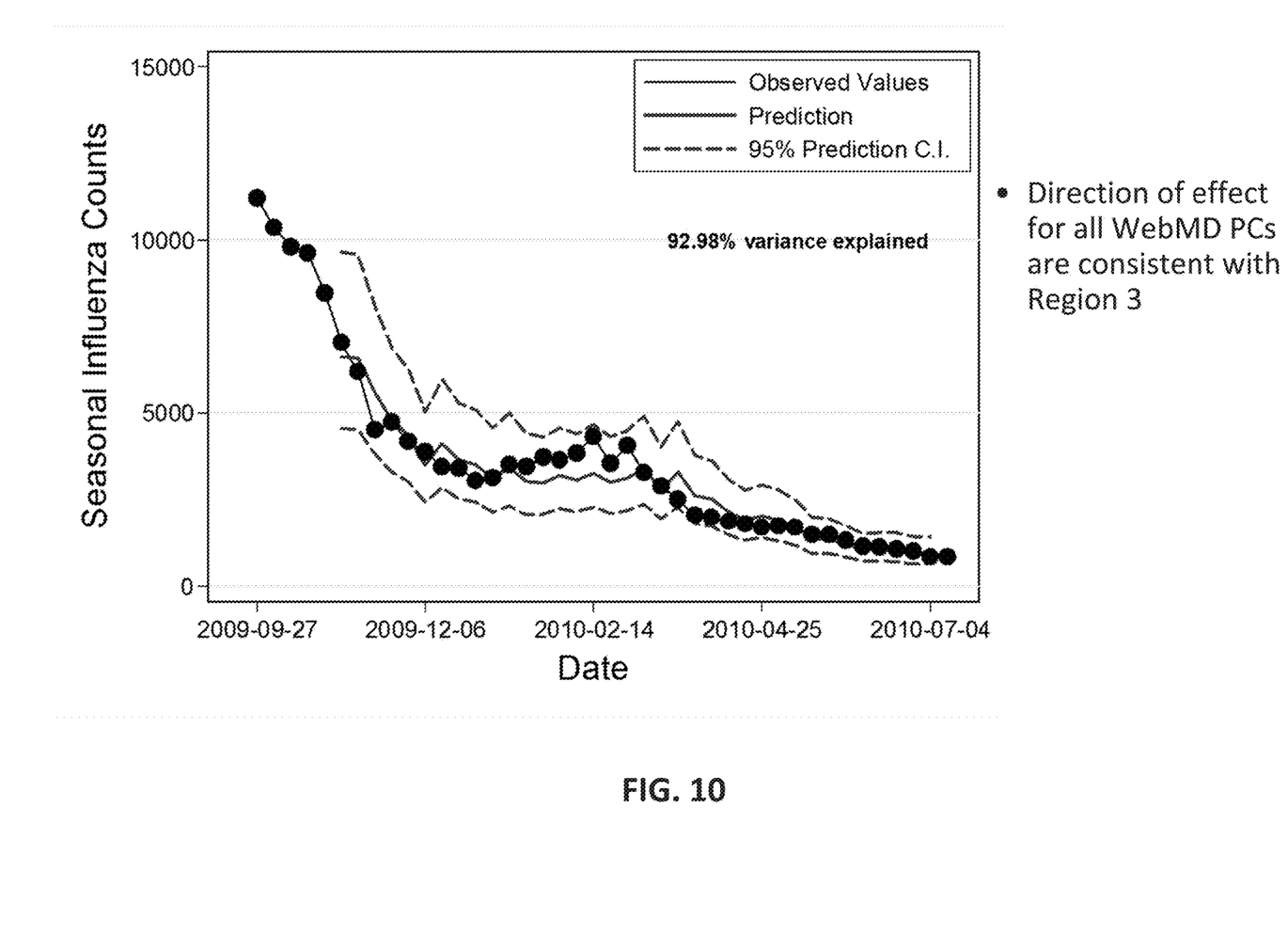
FIG. 10 is a graph of the prediction validation of the system according to the second exemplary embodiment shown in FIG. 2 in HHS Region 4.
Figure 11:
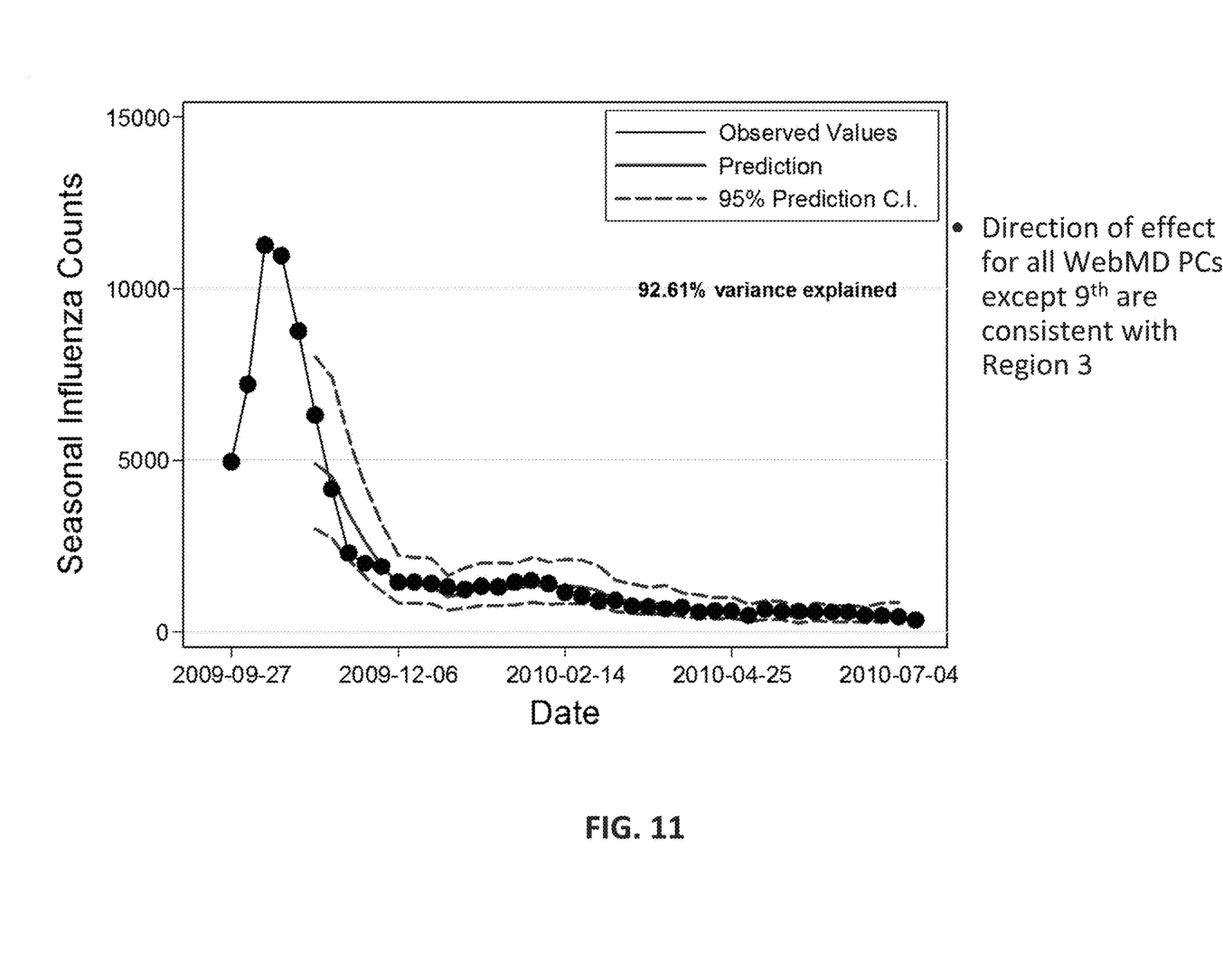
FIG. 11 is a graph of the prediction validation of the system according to the second exemplary embodiment shown in FIG. 2 in HHS Region 5.

With reference to FIGS. 9-11, a percent of variability explained (PVE) metric was constructed to measure the predictive ability of the model according to EQN 1:

$$PVE = 1 - \frac{\sum_t (Y_t - \hat{Y}_t)^{\wedge}2}{\sum_t (Y_t - \overline{Y}_t)^{\wedge}2} \qquad \text{EQN. 1}$$

This metric was compared with Google Flu Trend's mean reported correlation of 0.90 for weekly data. In FIG. 9, prediction of performance in region 3 is shown. Use of WebMD data shows an increase from 68.75% to 90.91% variance explained as calculated by EQN. 1.

With reference to FIG. 10, prediction of performance in region 4 is shown. A PVE value of 92.98% variance explained was obtained.

With reference to FIG. 11, prediction of performance in region 5 is shown. A PVE value of 92.61% variance explained was obtained.

It will be appreciated that various of the above-disclosed and other features and functions, or alternatives thereof, may be desirably combined into many other different systems or applications. It will be further appreciated that various presently unforeseen or unanticipated alternatives, modifications, variations or improvements therein may be subsequently made by those skilled in the art which are also intended to be encompassed by the following claims.

The invention claimed is:

1. A server computer for predicting the incidence of a disease or disorder, including:
   at least one processor and associated memory; and
   a communication interface configured to receive a plurality of structured symptom datasets generated by a web-based symptom checker in response to a corresponding plurality of symptom queries initiated by one or more persons inquiring about symptoms of illness from at least one user device over a distributed computer network, the plurality of structured symptom datasets received by the server computer from the web-based symptom checker via the distributed computer network, and the plurality of structured symptom datasets received prior to a change in public interaction with the distributed computer network;
   wherein the at least one processor is configured to process the plurality of structured symptom datasets using a dataset algorithm to produce a multivariate dataset from the plurality of structured datasets representing medically-relevant symptom counts with geographical and temporal characteristics;
   wherein the at least one processor is configured to filter the medically-relevant symptom counts to create subsets of the multivariate dataset based on previously indicated symptoms associated with at least one previously indicated illness;
   wherein the at least one processor is configured to process the subsets of the multivariate dataset using a feature construction algorithm to create orthogonal symbols representative of at least one illness;
   wherein the at least one processor is configured to create a time series model for the at least one illness based on the orthogonal symbols and historical illness incidence data associated with the at least one illness, the historical illness incidence data having been generated by at least one sentinel provider and being accessible to the at least one processor via the communication interface;
   wherein the at least one processor is configured to apply the time series model to new illness incidence data associated with the at least one illness to predict a future incidence of the at least one illness, the new illness incidence data having been generated by one or more sentinel providers and being accessible to the at least one processor via the communication interface; and
   wherein the at least one processor is configured to output a geographical and temporal early warning of the at least one illness in response to the application of the time series model to the new illness incidence data.

2. The server computer according to claim 1, wherein the historical illness incidence data includes past weekly illness incidence data.

3. The server computer according to claim 1, wherein, in conjunction with using the feature construction algorithm, the at least one processor is configured to perform a principle component analysis (PCA).

4. The server computer according to claim 1, wherein the web-based symptom checker comprises a WebMD Symptom Checker.

5. A method for predicting the incidence of a disease or disorder, the method comprising:
   receiving a plurality of structured symptom datasets at a server computer, the plurality of structured symptom datasets having been generated by a web-based symptom checker in response to a corresponding plurality of symptom queries initiated by one or more persons inquiring about symptoms of illness from at least one user device over a distributed computer network, the plurality of structured symptom datasets received by the server computer from the web-based symptom checker via the distributed computer network, and the plurality of structured symptom datasets received prior to a change in public interaction with the distributed computer network;
   processing the plurality of structured symptom datasets at the server computer using a dataset algorithm to produce a multivariate dataset from the plurality of structured symptom datasets representing medically-relevant symptom counts with geographical and temporal characteristics;
   processing the multivariate dataset at the server computer using a feature construction algorithm to create orthogonal symbols representative of at least one illness;
   creating a time series model for the at least one illness at the server computer based on the orthogonal symbols and historical illness incidence data associated with the at least one illness, the historical illness incidence data having been generated by at least one sentinel provider and being accessible to the server computer;

applying the time series model to new illness incidence data associated with the at least one illness at the server computer to predict a future incidence of the at least one illness, the new illness incidence data having been generated by one or more sentinel providers and being accessible to the server computer; and outputting a geographical and temporal early warning of the at least one illness in response to the application of the time series model to the new illness incidence data.

6. The method according to claim 5, further comprising:
performing a principle component analysis (PCA) in conjunction with using the feature construction algorithm.

7. The method according to claim 5, further including:
receiving filter selections at the server computer from a supervisor device, the filter selections being associated with control of the server computer in conjunction with at least one of the processing of the plurality of structured symptom datasets, the processing of the multivariate dataset, and the creating of the time series model.

8. The method according to claim 5, further including:
adjusting a time step lag in the time series model to prior to predicting the future incidence of the at least one illness to account for reporting lags in the historical illness incidence data.

9. The method according to claim 5, further including:
filtering the medically-relevant symptom count to create subsets of the multivariate dataset based on previously indicated symptoms associated with at least one previously indicated illness;
wherein the processing of the multivariate dataset is performed on the subsets of the multivariate dataset.

10. The method according to claim 5, wherein the plurality of structured symptom datasets include a plurality of WebMD Symptom Checker structured datasets.

11. A non-transitory computer readable medium storing program instructions that, when executed by a processor, cause a processor-controlled server computer to perform a method for predicting the incidence of a disease or disorder, the method comprising:
receiving a plurality of structured symptom datasets at a server computer, the plurality of structured symptom datasets having been generated by a web-based symptom checker in response to a corresponding plurality of symptom queries initiated by one or more person inquiring about symptoms of illness from at least one user device over a distributed computer network, the plurality of structured symptom datasets received by the server computer from the web-based symptom checker via the distributed computer network, and the plurality of structured symptom datasets received prior to a change in public interaction with the distributed computer network;
processing the plurality of structured symptom datasets at the server computer using a dataset algorithm to produce a multivariate dataset from the plurality of structured symptom datasets representing medically-relevant symptom counts with geographical and temporal characteristics;
filtering the medically-relevant symptom counts to create subsets of the multivariate dataset based on previously indicated symptoms associated with at least one previously indicated illness;
processing the subsets of the multivariate dataset at the server computer using a feature construction algorithm to create orthogonal symbols representative of at least one illness;
creating a time series model for the at least one illness at the server computer based on the orthogonal symbols and historical illness incidence data associated with the at least one illness, the historical illness incidence data having been generated by at least one sentinel provider and being accessible to the server computer;
applying the time series model to new illness incidence data associated with the at least one illness at the server computer to predict a future incidence of the at least one illness, the new illness incidence data having been generated by one or more sentinel providers and being accessible to the server computer; and
outputting a geographical and temporal early warning of the at least one illness in response to the application of the time series model to the new illness incidence data.

12. The method of claim 5, wherein the historical illness incidence data is based on a weekly time interval.

13. The method of claim 5, wherein the at least one illness includes an influenza like illness (ILI).

14. The method of claim 5, wherein the processing associated with the feature construction algorithm comprises:
performing a principal component analysis (PCA) on the medically-relevant symptom counts including symptom counts for: (1) body aches, (2) chills, (3) cough, (4) diarrhea, (5) difficulty breathing through nose, (6) fatigue, (7) fever, (8) headache, (9) worst headache, (10) joint ache, (11) nausea or vomiting, (12) runny nose, (13) shaking chills, and (14) sore throat.

15. The method of claim 5, wherein the processing associated with the feature construction algorithm comprises:
performing a principal component analysis (PCA) on the medically-relevant symptom counts of the multivariate dataset representing counts of symptoms associated with the plurality of structured symptom datasets.

16. The method of claim 5, wherein the plurality of structured symptom datasets are obtained from an Internet reporter source that provides structured health-related data.

17. The method of claim 5, wherein the plurality of structured symptom datasets are obtained from an Internet reporter source that stores data generated by symptom queries.

18. The server computer according to claim 1, wherein the web-based symptom checker comprises an on-line symptom checking diagnostic tool.

19. The server computer according to claim 1, wherein the at least one processor is configured to receive filter selections from a supervisor device via the communication interface, the filter selections being associated with control of the at least one processor in conjunction with at least one of the processing of the plurality of structured symptom datasets, the processing of the multivariate dataset, and the creating of the time series model.

20. The method according to claim 5, wherein the plurality of structured symptom datasets include a plurality of on-line symptom checking diagnostic tool datasets.

21. The server computer according to claim 1, wherein the change in public interaction with the distributed computer network corresponds to user interaction with the distributed computer network following public knowledge of the illness.

22. The method according to claim 5, wherein the change in public interaction with the distributed computer network corresponds to user interaction with the distributed computer network following public knowledge of the illness.

\* \* \* \* \*